(12) United States Patent
Parate et al.

(10) Patent No.: US 11,127,501 B2
(45) Date of Patent: Sep. 21, 2021

(54) SYSTEMS AND METHODS FOR HEALTH MONITORING

(71) Applicant: Lumme Health, Inc., Dover, DE (US)

(72) Inventors: Abhinav Parate, Worcester, MA (US); Akshaya Shanmugam, Amherst, MA (US); Deepak Ganesan, Amherst, MA (US); Christopher Donovan Salthouse, Newton, MA (US); Sherry Ann McKee, Guilford, CT (US)

(73) Assignee: Lumme Health, Inc., Dover, DE (US)

( * ) Notice: Subject to any disclaimer, the term of this patent is extended or adjusted under 35 U.S.C. 154(b) by 808 days.

(21) Appl. No.: 15/692,967

(22) Filed: Aug. 31, 2017

(65) Prior Publication Data

US 2018/0068080 A1 Mar. 8, 2018

Related U.S. Application Data

(60) Provisional application No. 62/383,059, filed on Sep. 2, 2016.

(51) Int. Cl.
*G16H 40/67* (2018.01)
*G16H 40/63* (2018.01)
(Continued)

(52) U.S. Cl.
CPC ............. *G16H 40/67* (2018.01); *G16H 40/63* (2018.01); *G16H 50/20* (2018.01); *G16H 50/50* (2018.01); *G16H 80/00* (2018.01); *G06Q 10/109* (2013.01)

(58) Field of Classification Search
CPC ..... A61B 5/681; A61B 5/0022; A61B 5/1112; A61B 2562/0219; A61B 5/6824;
(Continued)

(56) References Cited

U.S. PATENT DOCUMENTS

2008/0208015 A1 8/2008 Morris et al.
2014/0052465 A1 2/2014 Madan et al.
(Continued)

FOREIGN PATENT DOCUMENTS

WO WO 2016/100368 A1 6/2016
WO WO-2017129946 A1 * 8/2017 ............... A61B 5/11

OTHER PUBLICATIONS

Rahman, M. M. (2016). Improving quality and quantity of data captured via wearable physiological sensors: A step towards precision medicine initiative (Order No. 10296290). Available from ProQuest Dissertations and Theses Professional. (1845054264). (Year: 2016).*
Parate, Designing Efficient and Accurate Behavior-Aware Mobile Systems. Dissertation submitted to University of Massachusetts Amherst. Sep. 2014. 189 pages.
International Search Report and Written Opinion for International Application No. PCT/US2017/49576 dated Nov. 16, 2017.
(Continued)

*Primary Examiner* — Joseph D Burgess
(74) *Attorney, Agent, or Firm* — Wolf, Greenfield & Sacks, P.C.

(57) ABSTRACT

Behavioral intervention improves the efficacy of treatments designed to encourage healthy behaviors such as smoking cessation, adherence to food regimen after surgeries, and avoiding overeating. Aspects of the present disclosure relate to a health monitoring system that leverages wearable sensors, mobile devices (e.g. smartphones), and computer-based servers to monitor the health of a user and provide intervention at opportune moments to encourage healthy behavior. This system provides a scalable and cost-efficient way for health care providers to monitor the behavior of many users and encourage healthy behavior as appropriate.

20 Claims, 3 Drawing Sheets

(51) Int. Cl.
*G16H 50/50* (2018.01)
*G16H 80/00* (2018.01)
*G16H 50/20* (2018.01)
*G06Q 10/10* (2012.01)

(58) Field of Classification Search
CPC ......... A61B 5/11; A61B 5/746; A61B 5/0004; A61B 5/1114; A61B 2010/0009; A61B 2010/0087; A61B 5/0002; A61B 5/097; G16H 40/67; G16H 20/30; G16H 50/20; G16H 80/00; G16H 10/60; G16H 50/30; G16H 50/50; G16H 20/60; G16H 50/70; G16H 70/60; G06F 19/00; G06F 19/3481; G06F 19/30; G06F 1/163; G06F 3/017; G06F 3/0346; G06F 16/29; G06F 2221/2111
See application file for complete search history.

(56) References Cited

U.S. PATENT DOCUMENTS

| | | | |
|---|---|---|---|
| 2016/0086500 A1* | 3/2016 | Kaleal, III | G06T 19/00 434/257 |
| 2017/0039045 A1* | 2/2017 | Abrahami | A61B 5/1118 |
| 2017/0220772 A1* | 8/2017 | Vleugels | G16H 70/60 |
| 2017/0262064 A1* | 9/2017 | Ofir | G06F 3/0346 |

OTHER PUBLICATIONS

Parate et al., RisQ: Recognizing Smoking Gestures with Inertial Sensors on a Wristband. MobiSys. Jun. 2014. 14 pages.
Extended European Search Report for European Application No. 17847537.2 dated Mar. 24, 2020.
International Preliminary Report on Patentability for International Application No. PCT/US2017/049576 dated Mar. 14, 2019.

* cited by examiner

SYSTEMS AND METHODS FOR HEALTH MONITORING

RELATED APPLICATIONS

This Application claims priority under 35 U.S.C. § 119(e) to U.S. Provisional Application Ser. No. 62/383,059, entitled "SYSTEMS AND METHODS FOR HEALTH MONITORING" filed on Sep. 2, 2016, which is herein incorporated by reference in its entirety.

FEDERALLY SPONSORED RESEARCH

This invention was made with Government support from the National Cancer Institute under contract number HHSN261201500016C. The Government may have certain rights to this invention.

BACKGROUND

People may engage in various unhealthy behaviors such as, for example, smoking, using chewing tobacco, illicit drug use, and overeating. Each person may have unique triggers that increase the likelihood of performing a particular unhealthy activity. For example, a person may be more inclined to smoke a cigarette and/or use chewing tobacco immediately after consuming alcohol. In another example, a person may be more inclined to overeat in response to experiencing periods of high stress.

SUMMARY

According to at least one aspect, a health monitoring system is provided. The health monitoring system may include a wearable sensor configured to generate information indicative of at least one parameter of a user and a mobile device including at least one processor communicatively coupled to the wearable sensor and at least one computer-readable storage medium. The at least one computer-readable storage medium may store instructions which program the at least one processor to receive the information indicative of at least one parameter of the user, identify a behavior performed by the user based on the information indicative of at least one parameter of the user, obtain contextual information regarding the identified behavior, determine whether to intervene based on at least one of the identified behavior and the contextual information regarding the identified behavior, and intervene with the user responsive to a determination to intervene.

In some embodiments, the mobile device is a wearable device and the wearable sensor is integrated into the wearable device. In some embodiments, the wearable sensor includes at least one of: an accelerometer, a blood pressure sensor, a pulse oximeter, a galvanic skin response sensor, and a body temperature sensor. In some embodiments, the identified behavior includes at least one of: smoking, using chewing tobacco, consuming alcohol, eating, drinking, overeating, using illicit drugs, and consuming a liquid diet.

In some embodiments, the mobile device includes a sensor configured to generate information indicative of at least one parameter of an environment of the user and the at least one processor of the mobile device is further programmed to obtain the contextual information regarding the identified behavior from the information indicative of at least one parameter of the environment of the user. In these embodiments, sensor may include a global positioning system (GPS) receiver and the contextual information includes a location of the user when the user engaged in the identified behavior. In these embodiments, the sensor may include a time-keeping device and the contextual information includes a time of day when the user engaged in the identified behavior.

In some embodiments, the at least one processor of the mobile device is further programmed to determine whether to intervene at least in part by comparing a rule defining an action to be performed in response to detecting one or more conditions to at least one of the identified behavior and the contextual information regarding the identified behavior. In these embodiments, the at least one processor of the mobile device may be further programmed to intervene with the user at least in part by performing the action in the rule. In these embodiments, the health monitoring system may further include a server in communication with the mobile device and be configured to generate the rule and transmit the rule to the mobile device. In these embodiments, the mobile device may be configured to transmit the identified behavior and the contextual information regarding the identified behavior to the server and the server may be further configured to generate the rule based on the identified behavior and the contextual information regarding the identified behavior.

In some embodiments, the mobile device further includes a display coupled to the at least one processor and the at least one processor of the mobile device is further programmed to intervene with the user at least in part by displaying a message via the display.

According to at least one aspect, a method of monitoring a health of a user is provided. The method may include sensing, by a wearable sensor, information indicative of at least one parameter of the user, identifying, by a computing device in communication with the wearable sensor, a behavior performed by the user based on the information indicative of at least one parameter of the user, obtaining, by the computing device, contextual information regarding the identified behavior, determining, by the computing device, whether to intervene based on at least one of the identified behavior and the contextual information regarding the identified behavior, and intervening, by the computing device, with the user responsive to a determination to intervene. The computing device may be, for example, a mobile device, one or more servers, and/or a mobile device working in-conjunction with one or more servers.

In some embodiments, the wearable sensor includes at least one of: an accelerometer, a blood pressure sensor, a pulse oximeter, a galvanic skin response sensor, and a body temperature sensor. In some embodiments, the identified behavior includes at least one of: smoking, using chewing tobacco, consuming alcohol, eating, drinking, overeating, using illicit drugs, and consuming a liquid diet.

In some embodiments, the method further includes sensing at least one parameter of an environment of the user by a sensor and the act of obtaining the contextual information regarding the identified behavior includes obtaining the contextual information regarding the identified behavior from the information indicative of at least one parameter of the environment of the user. In these embodiments, the sensor may include a global positioning system (GPS) receiver and the contextual information includes a location of the user when the user engaged in the identified behavior. In these embodiments, the sensor may include a time-keeping device and the contextual information includes a time of day when the user engaged in the identified behavior.

In some embodiments, the act of determining whether to intervene includes comparing a rule defining an action to be performed in response to detecting one or more conditions to at least one of the identified behavior and the contextual information regarding the identified behavior. In these embodiments, the act of intervening with the user may include performing the action in the rule. In these embodiments, the method may further include generating the rule based on the identified behavior and the contextual information regarding the identified behavior.

In some embodiments, the mobile device may further include a display coupled to the at least one processor and intervening with the user includes displaying a message via the display.

According to at least one aspect, a health monitoring system is provided. The health monitoring system may include a communication interface configured to communicate with a mobile device associated with a user, at least one processor communicatively coupled to the communication interface, and at least one computer-readable storage medium. The at least one computer-readable storage medium may store instructions which program the at least one processor to receive at least one identified behavior performed by the user and contextual information regarding the at least one identified behavior from the mobile device, generate at least one rule defining an action to be performed in response to detecting one or more conditions based on the at least one identified behavior performed by the user and contextual information regarding the at least one identified behavior, and send the at least one rule to the mobile device.

In some embodiments, the communication interface is configured to communicate with a plurality of mobile devices associated with a respective plurality of users including the mobile device associated with the user and the at least one processor is further programmed to receive a plurality of identified behaviors performed by the plurality of users. In these embodiments, the health monitoring system may further include a web-interface accessible by a health coach of a subset of the plurality of users over the internet that is configured to display information indicative of the plurality of identified behaviors performed by the subset of the plurality of users.

According to at least one aspect, a health monitoring system is provided. The health monitoring system comprises a wearable device configured to be disposed about a wrist of a user. The wearable device comprises an accelerometer configured to generate information indicative of a movement of the user's wrist. The health monitoring system further comprises a mobile device. The mobile device comprises at least one processor communicatively coupled to the wearable device, a display coupled to the at least one processor, a sensor coupled to the at least one processor and configured to generate information indicative of at least one parameter of an environment of the user, and at least one computer-readable storage medium storing instructions which program the at least one processor to: receive the information indicative of the movement of the user's wrist, identify a smoking behavior performed by the user based on the information indicative of the movement of the user's wrist, obtain the contextual information regarding the identified smoking behavior from the information indicative of at least one parameter of the environment of the user, determine whether to intervene based on at least one of the identified smoking behavior and the contextual information regarding the identified smoking behavior, and intervene with the user at least in part by displaying a message via the display responsive to a determination to intervene.

Features of the above-described embodiments may be used alone or in any suitable combination.

The foregoing is a non-limiting summary of the invention, which is defined by the appended claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
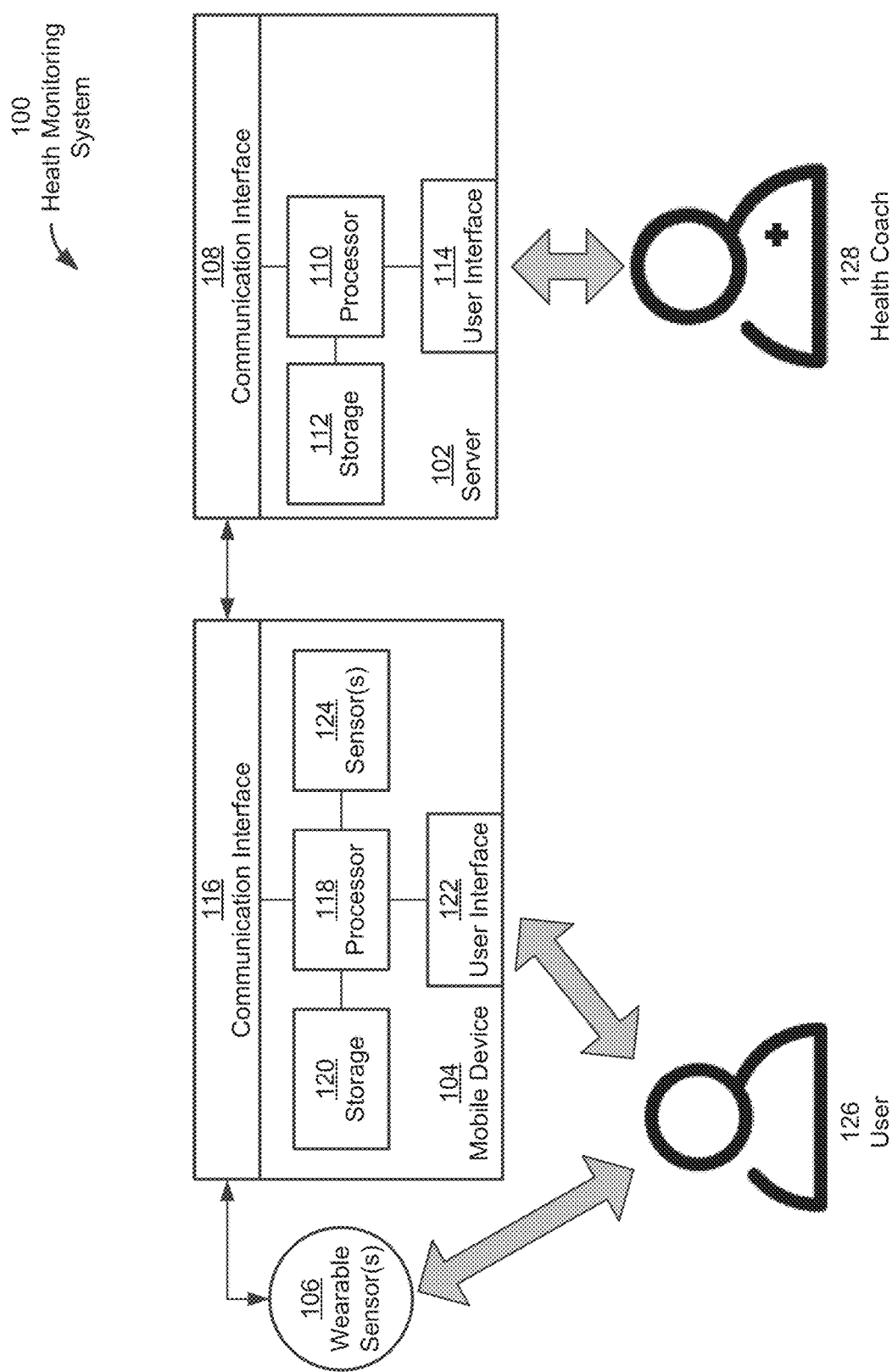
FIG. 1 is a block diagram of an example health monitoring system, according to some embodiments.

The inventors have appreciated that conventional systems that monitor a behavior of an individual typically require the individual to manually record occurrences of the behavior. For example, a conventional system that tracks eating behaviors of an individual typically requires the individual manually input information regarding the particular food items they consumed. The manually input information, however, is likely not an accurate reflection of the particular behaviors engaged in by the individual because individuals have a natural tendency to under-report bad behaviors and/or over-report good behaviors. Thereby, any feedback provided to the individual by the system may be erroneous. For example, the system may report that an individual is on-track to lose weight based on their manually input diet information when, in fact, they are on track to gain 10 pounds.

Accordingly, the inventors have devised new health monitoring systems that improve upon convention systems by automatically (and accurately) tracking and identifying the behaviors engaged in by an individual. These health monitoring systems may employ, for example, sensor information from one or more portable electronic devices, such as smartphones and activity monitoring devices, that may be carried by an individual to automatically track and identify these behaviors. Thereby, the information gathered by the health monitoring system regarding the behaviors engaged in by an individual is more accurate than in convention systems. Further, the feedback provided to the individual regarding their behaviors may be more truthful than that provided by conventional systems.

Aspects of the present disclosure relate to health monitoring systems that monitor the health related behaviors performed by an individual, identify potential triggers that increase the risk that the individual will engage in unhealthy behaviors, and/or intervene at opportune times to encourage the individual to engage in healthy behaviors. In some embodiments, the health monitoring systems may leverage information from various sensors to identify specific behaviors of the individual in addition to contextual information when the individual is engaging in the particular behavior. For example, the health monitoring system may use information from an accelerometer disposed around a wrist of a user to determine whether the user is engaging in a smoking behavior and information from a global positioning system (GPS) receiver in a mobile phone of the user to determine where the user is smoking. The behavior information coupled with the contextual information may, in turn, be employed to identify patterns of behavior. For example, a user may frequently smoke a cigarette after going to a particular location. The health monitoring system may use these recognized patterns to intervene at opportune times to encourage the user to engage in healthy behavior and/or discourage unhealthy behavior. For example, the health monitoring system may trigger an encouraging notification informing the user of the time since they last smoked a cigarette when the user is approaching the location where they typically smoke.

Embodiments of a health monitoring systems disclosed herein offer numerous advantages relative to conventional systems. For example, the health monitoring system may provide real-time information to the user regarding their behaviors, such as how many times they have smoked recently or how much time has passed since they last smoked. Further, contextual information may be gathered in conjunction with information regarding the particular behavior being performed by a user to gain a better understanding of the behavior and any potential triggers for the user. Thereby, the timing and/or type of intervention employed to encourage the user to engage in healthy behavior may be specifically tailored to each individual to increase effectiveness based on the collected information. The customized timing and/or type of intervention may be partially (or completely) automated to allow a single health care provider to help more users simultaneously.

In some embodiments, the health monitoring system may leverage existing electronic devices already owned and used by countless individuals. In these embodiments, the health monitoring system may gather sensor information from sensors integrated into various wearable devices, such as exercise monitors and smartwatches, to identify particular behaviors. For example, the health monitoring system may monitor hand-to-mouth movements of a user to determine whether the user is smoking through sensor data from an accelerometer in a wearable device disposed around the wrist of the user, such as a NIKE FITBIT and an APPLE WATCH. The health monitoring system may leverage a smartphone (or other computing device) frequently carried by an individual to gather contextual information regarding the behavior. For example, the health monitoring system may obtain contextual information from a calendar of the user on the smartphone, text messages sent or received on the smartphone, and phone calls made or received on the smartphone. In other examples, the health monitoring system may obtain information from sensors integrated into the smartphone such as accelerometers, GPS receivers, gyroscopes, microphones, light sensors, and/or proximity sensors. Further, the computing resources of the smartphone may be used to store and/or analyze the information collected from the sensors integrated into the wearable devices and/or the smartphone itself.

In some embodiments, the health monitoring system may identify particular behaviors performed by the users based on the received sensor information. In these embodiments, the health monitoring system may build a model of the expected features in the output of one or more sensors when the user is performing a particular behavior and compare the generated model with the sensor information being received and/or identified features in the output of the one or more sensors. For example, the health monitoring system may include an accelerometer disposed about a wrist of the user in a wearable device. In this example, the health monitoring system may construct a model of expected features in the output of the accelerometer when the user is smoking and compare the model with the received accelerometer data and/or identified features in the output of the accelerometer data to determine whether the user is smoking.

In some embodiments, the health monitoring system may intervene at opportune times to encourage the user to engage in healthy behavior and/or discourage unhealthy behavior. In these embodiments, the data collected by the health monitoring system may be analyzed to identify scenarios of elevated risk for the user engaging in unhealthy behavior and generate rules defining an action to be performed in response to detecting one or more conditions. For example, a rule may be generated indicating that a notification should be provided to a user if the user smokes more than five cigarettes in a twelve hour period. The generated rules may be employed by a mobile computing device, such as a smartphone of the user, to provide the appropriate intervention. For example, the mobile computing device of the user may monitor received sensor information and determine whether the sensor information matches the conditions identified in a rule. In this example, the mobile computing device may perform the action in the rule responsive to the sensor information matching the conditions in the rule. The rules may be generated automatically by the health monitoring system and/or with assistance from a healthcare provider. For example, the identified patterns of behavior may be presented to a healthcare provider and the healthcare provider may, in turn, specify particular rules for a user based on the identified trends.

The aspects and embodiments described above, as well as additional aspects and embodiments, are described further below. These aspects and/or embodiments may be used individually, all together, or in any combination of two or more, as the application is not limited in this respect.

Aspects of the present disclosure relate to a system that may continuously monitor a range of behaviors and contexts surrounding the behaviors using sensors available on mobile devices (e.g. smartphone) and/or wearable devices (e.g. smartwatch, fitness bands). For example, the health monitoring system may detect a behavior, such as smoking, using chewing tobacco, consuming alcohol, eating, drinking, overeating, using illicit drugs, and/or consuming a liquid diet, by comparing the output of sensors available on a smartwatch, such as an accelerometer, with a model of the expected output and/or features in the output of the sensors during the behavior. The health monitoring system may additionally obtain contextual information when the user is engaging in the identified behavior, such as a location of the user, a time of day, an ambient light level, and an ambient noise level, using the mobile device. The gathered information may be analyzed with the mobile device and/or a server in communication with the mobile device to determine the appropriate intervention to provide to the user to discourage (or encourage) a particular behavior. For example, the mobile device may transmit the collected information to a server and the server may identify patterns in the collected information, such as the user always smokes when the user is at a particular location. In this example, the server may generate rules defining an action to be performed by the mobile device in response to detecting one or more conditions to discourage (or encourage) a particular behavior and provide these rules to the mobile device, such as a rule indicating that an encouraging message should be provided to the user when the user is approaching a particular location. It should be appreciated that the rules may be generated automatically via the server and/or in-conjunction with a health coach of the user.

An example of such a health monitoring system is shown in FIG. 1 by health monitoring system 100. As shown, the health monitoring system includes a server 102 comprising a communication interface 108, a processor 110, storage 112, and a user interface 114. The server 102 may be in communication with a mobile device 104 that includes a communication interface 116, a processor 118, storage 120, a user interface 122, and sensor(s) 124. The mobile device 104 may be in communication with one or more wearable sensor(s) 106.

The wearable sensor(s) 106 may generate sensor information indicative of at least one parameter of the user 126 that may be employed to identify behaviors performed by the user 126. In some embodiments, the wearable sensor(s) 106 may be disposed about various body parts, such as a wrist, a bicep, an ankle, and a torso, of the user 126. For example, the wearable sensor(s) 106 may be disposed around a wrist of the user 126 and include an accelerometer configured to generate information indicative of arm movements performed by the user 126. In this example, the information indicative of arm movements performed by the user 126 may be employed by the mobile device 104 to determine whether the user 126 is smoking. It should be appreciated that the wearable sensor(s) 106 may include sensors separate from accelerometers or other devices configured to detect movement. For example, the wearable sensor(s) 106 may include a blood pressure sensor, a pulse oximeter, a galvanic skin response sensor, and/or a body temperature sensor.

In some embodiments, the wearable sensor(s) 106 may communicate sensor information to the mobile device 104. The communication between the wearable sensor(s) 106 and the mobile device 104 may be over a wireless communication channel and/or a wired communication channel. The wearable sensor(s) 106 may use any one of a variety of protocols to communicate with the mobile device 104. For example, the wearable sensor(s) 106 may wirelessly communicate with the mobile device 104 using BLUETOOTH and/or ZIGBEE protocols.

It should be appreciated that one or more of the wearable sensor(s) 106 may be integrated into a computer-enabled wearable device in some embodiments. For example, one or more of the wearable sensor(s) 106 may be integrated into a smartwatch, such as the APPLE WATCH. In these embodiments, the wearable device may perform any portion (or all) of the functions attributed to the mobile device 104. For example, the wearable device may be disposed about a wrist of the user 126 and be configured to read the output of an accelerometer integrated into the wearable device and determine whether the user 126 is engaging in a particular behavior, such as smoking. In this example, the wearable device may provide an indication of whether the user 126 is engaging in the particular behavior to the mobile device 104 in place of (or in conjunction with) the output of the accelerometer. In another example, the wearable device may include the wearable sensor(s) 106 and perform all of the functions of the mobile device 104. In this example, the wearable device may directly communicate with the server 102.

The mobile device 104 may be, for example, a portable computer-enabled device associated with the user 126 such as a smartphone or a tablet. The mobile device 104 may include various components to perform the health monitoring functions described herein. For example, the mobile device 104 may include a processor 118 coupled to a communication interface 116, storage 120, a user interface 122 and/or sensor(s) 124. The processor 118 may be configured to manipulate data in accordance with a set of instructions. For example, the processor 118 may read a set of instructions stored in the storage 120 and manipulate data in accordance with the stored set of instructions. The processor 118 may be, for example, any commercially available processor such as those available from QUALCOMM and MOTOROLA. The communication interface 116 may facilitate wireless and/or wired communication between the mobile device 104 and external devices, such as the server 102 and/or the wearable sensor(s) 106. The communication interface 116 may be capable of communicating with external devices using, for example, BLUETOOTH, BLUETOOTH SMART, ZIGBEE, wireless Ethernet, cellular 3G, and/or cellular 4G. The storage 120 may include a computer readable and writeable nonvolatile recording medium in which computer executable instructions may be stored that define a program to be executed by the processor 118. For example, the storage 120 may include a non-transitory computer readable medium. The user interface 122 may permit an individual, such as user 126, to interact with the mobile device 104. For example, the user interface 122 may include a display, a touch screen, a speaker, a button, a knob, a dial, a keyboard, a vibration device, and/or a touchpad. The sensor(s) 124 may be, for example, any physical sensors integrated into the mobile device 104 such as accelerometers, GPS receivers, gyroscopes, microphones, light sensors, and/or proximity sensors and/or any logical sensors such as sensors that monitor semantic locations and/or physical activity like walking or driving.

The mobile device 104 may be configured to gather information from the wearable sensor(s) 106 and/or sensor(s) 124 integrated into the mobile device 104 to, for example, identify behaviors engaged in by the user and/or identify contextual information when the user 126 is engaging in these behaviors. In some embodiments, the mobile device 104 may receive sensor information from the wearable sensor 106 and analyze the received sensor information to identify behaviors performed by the user 126. In these embodiments, the mobile device 104 may obtain contextual information from any of a variety of available sources. For example, the mobile device 104 may obtain information from a calendar of the individual to identify the schedule of the user 126. In another example, the mobile device may obtain contextual information from sensor(s) 124 integrated into the mobile device 104 such as GPS receivers, accelerometers, microphones, and light sensors.

In some embodiments, the mobile device 104 may walk the user 126 through various training exercises during setup of the monitoring system 100. These training exercises may increase the accuracy of detecting the mobile device 104. For example, the mobile device 104 may be configured to detect the user 126 engaging in a smoking behavior by reading the output of an accelerometer disposed about a wrist of the user 126. In this example, the mobile device 104 may request the user 126 to hold a cigarette and pretend to smoke as they normally would. The mobile device 104 may monitor the output of the accelerometer during this training exercise and construct a model of the behavior. The model of the behavior may be employed by the mobile device 104 to more accurately determine whether the user 126 is smoking based on the output of the accelerometer.

The sensor(s) 124 may provide information indicative of at least one parameter of an environment of the user 126 that may be used to generate contextual information associated with a particular behavior. The contextual information associated with a particular behavior may be leveraged to, for example, identify scenarios of elevated risk for the user engaging in a particular behavior. For example, the user 126 may engage in a particular behavior when the user 126 goes to a location and/or interacts with particular people. Any of a variety of sensors and/or sensing devices may be integrated into the mobile device 104 as the sensor(s) 124. For example, the contextual information may include a location of the user 126 when the user 126 is engaging in a particular behavior (e.g., smoking) and the sensor(s) 124 may include a GPS receiver. In this example, the mobile device 104 may read the GPS receiver when the mobile device 104 detects the user engaging in a particular behavior. In another example, the contextual information includes people located nearby the user 126 when the user is engaging in a particular behavior (e.g., using illicit drugs) and the sensor(s) 124 may include a BLUETOOTH device configured to establish a wireless connection with another BLUETOOTH enabled device. In this example, the BLUETOOTH device may interrogate nearby BLUETOOTH enabled devices, such as nearby smartphones, to obtain identifier values that may be employed to identify individuals proximate the user 126. It should be appreciated that still yet other sensors may be employed as sensor(s) 124 to generate other contextual information including, for example, a microphone to identify people near the user 126 and/or topics of conversation of the user 126, an accelerometer to determine whether the user is driving or walking, and a time-keeping device to determine the time of day. Further, the mobile device 104 may obtain contextual information from sources other than integrated sensors 124 such as a calendar of the user.

In some embodiments, the mobile device 104 may intervene at opportune times to discourage the user from engaging in unhealthy behaviors. In these embodiments, the mobile device 104 may apply one or more rules each defining a particular action that should be taken by the mobile device 104 in response to detecting one or more conditions. For example, the mobile device 104 may apply a rule indicating that a message should be presented to the user 126 when the user 126 has spent 30 minutes at home and the time of day is between 3 pm and 4 pm in the afternoon. In another example, the mobile device 104 may apply a rule indicating that the user 126 should be prompted with a set of questions at 8 pm in the evening. The rules implemented by the mobile device 104 may be generated by the server 102 as discussed in more detail below. For example, the mobile device 104 may send collected information to the server 102 for analysis. The server 102 may, in turn, identify patterns in the collected information and automatically generate rules and/or generate the rules in-conjunction with a health coach 128 of the user 126.

The mobile device 104 may employ any suitable user interface 122 to intervene with the user 126. For example, the mobile device may display a particular notification via a display, vibrate a vibration device, and/or sound an alarm via a speaker in response to a particular set of conditions, such as being near a particular location. Additionally or alternatively, the mobile device 104 may initiate communication with an external system and/or a particular person. Such communication may be a voice call, an email, or a text message. For example, the mobile device 104 may initiate a call to the health coach 128 of the user 126 in response to a particular set of conditions.

The server 102 may be, for example, a computing device (or network of computing devices) with one or more fixed locations and/or more computing resources (e.g., faster processor) than the mobile device 104. The server 102 may include various components to analyze the data collected by the mobile device 104 and/or generate rules. For example, the mobile server 102 may include a processor 110 coupled to a communication interface 110, storage 112, and a user interface 114. The processor 110 may be configured to manipulate data in accordance with a set of instructions. For example, the processor 110 may read a set of instructions stored in the storage 112 and manipulate data in accordance with the stored set of instructions. The processor 110 may be, for example, any commercially available processor such as those available from INTEL and AMD. The communication interface 116 may facilitate wireless and/or wired communication between the server 102 and external devices, such as the mobile device 104. The communication interface 108 may be capable of communicating with external devices using, for example, wireless Ethernet, cellular 3G, and/or cellular 4G. The storage 112 may include a computer readable and writeable nonvolatile recording medium in which computer executable instructions are stored that define a program to be executed by the processor 110. For example, the storage 112 may include a non-transitory computer readable medium. The user interface 114 may permit an individual, such as health coach 128, to interact with the server 102. The user interface 114 may also permit a health coach 128 to communicate with one or more users 126 assigned to the heath coach 128. The user interface 114 may include various components such as a display, a touch screen, a speaker, a button, a knob, a dial, a keyboard, a vibration device, and/or a touchpad. It should be appreciated that the user interface 114 may be a web interface in some embodiments. In these embodiments, the web interface of the server 102 may be accessed over the internet via another computer system. For example, the health coach 128 may interact with the server 102 using a web-browser on another computing device (not shown) that is in communication with the server 102 via the internet. It should be appreciated that any of a variety of people associated with the user 126 may be the health coach 128. For example, the health coach 128 may be a caregiver, a family member, a physician, a friend, a therapist, an insurance provider, and/or a psychiatrist of the user 126.

In some embodiments, a single server 102 may be in communication with multiple mobile devices 104 and/or processing collected data for multiple users 126. In these embodiments, the user interface 114 may require entry of a user ID and/or a passphrase to view data associated with any user 126. In cases where a single health coach 128 is monitoring the activity of multiple users 126, the user interface 114 may permit the health coach 128 to view the data associated with all of the users 126 assigned to the particular health coach 128.

The server 102 may employ various machine learning techniques to extract behavioral patterns from the information associated with a user, such as the data received from the mobile device 104. For example, the server 102 may extract behavioral patterns identifying scenarios when the user 126 is highly likely to engage in a harmful behavior such as smoking a cigarette. In some embodiments, the server 102 may employ temporal rule mining techniques to identify patterns of events, such as walking to a particular location, that are correlated to a subsequent behavior, such as smoking. In other embodiments, the server 102 may employ Bayesian network based modeling to identify probabilistic relationships between various pieces of contextual information, such as the time of day, and a particular behavior, such as using chewing tobacco. It should be appreciated that still yet other techniques may be employed to identify patterns in the collected data.

As discussed above, the server 102 may generate the rules specifying the particular action that should be taken by the mobile device 104 to discourage (or encourage) a behavior and the particular set of conditions that should trigger the specified action. In some embodiments, the server 102 may identify one or more rules based on the identified patterns in the collected data. For example, the server 102 may identify a sequence of acts that frequently precede the user 126 engaging in an unhealthy behavior. In this example, the server 102 may construct a rule indicating that the mobile device 104 should issue a notification to the user 106 when all or a portion of the sequence of acts is detected. In other embodiments, the server 102 may generate rules with the assistance of the health coach 128. For example, the server 102 may display the collected data and/or any identified patterns to the health coach 128 via the user interface 114. In this example, the user interface 114 may permit the health coach 128 to create particular rules by specifying a particular action to be performed by the mobile device 104, such as opening a game, playing music, initiating a communication to another individual, displaying a message, and sounding an alert, when a particular set of conditions are met, such as the user being at a particular location.

It should be appreciated that the functionality attributed to the server 102 be performed in part (or entirely) by the mobile device 104 (or vice-versa) depending upon the particular implementation. For example, the mobile device 104 may have sufficient processing capability to identify patterns in the collected data and may identify the patterns locally without the server 102. In this example, the mobile device 104 may send the identified patterns and/or collected information to the server 102 to make the information accessible to the health coach 128 via the user interface 114. In another example, the mobile device 104 may have very limited processing capabilities and the mobile device 104 may pass on the collected information to the server 102 where the server 102 may apply the rules and send instructions to the mobile device regarding the particular actions to perform based on the rules. In yet another example, the mobile device 104 may identify behaviors and obtain contextual information and pass this information to the server 102 where the server 102 may apply the rules and send instructions to the mobile device regarding actions to perform.

Figure 2:
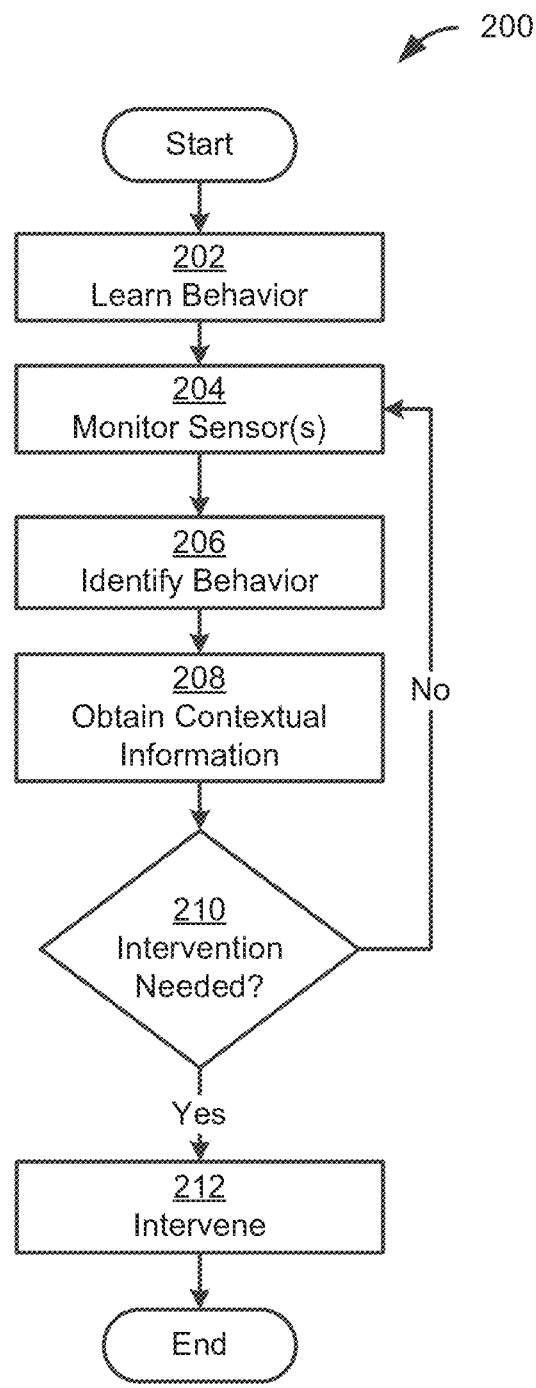
FIG. 2 is a flowchart of an example health monitoring process, according to some embodiments.

As discussed above, the health monitoring system described herein may monitor the behaviors performed by a user and intervene with the user at opportune times to discourage (or encourage) the user from engaging in a particular behavior. An example of such a health monitoring process that may be performed by, for example, a mobile device of a health monitoring system, such as mobile device 104 in health monitoring system 100, is illustrated by process 200 in FIG. 2.

In act 202, the mobile device may learn one or more behaviors of the user. For example, the mobile device may construct a model of a behavior and use the constructed model to subsequently identify the behavior. In some embodiments, the mobile device may request that the user perform (or pretend to perform) a particular behavior, such as smoking. In these embodiments, the mobile device may monitor the output of various sensors, such as an accelerometer disposed about a wrist of the user, while the user is performing the behavior and build a model of the behavior based on the sensed output. It should be appreciated that the mobile device may generate the model of the behavior locally and/or in-conjunction with a server. For example, the mobile device may transmit the collected sensor information to the server where the server may generate the model and transmit the generated model to the mobile device.

In act 204, the mobile device may monitor the output of one or more sensors that may be integrated into the mobile device and/or in communication with the mobile device. For example, the mobile device may wirelessly receive sensor information from a sensor (e.g., a wearable sensor) indicative of at least one parameter of the user, such as a movement of a body part of the user, a blood pressure of the user, a body temperature of the user, a galvanic skin response of the user, and/or an oxygen saturation of the user. Additionally or alternatively, the mobile device may gather sensor information from a sensor (e.g., a sensor integrated into the mobile device) that is indicative of the at least one parameter of an environment of the user, such as a location of the user, smartphones or other electronic devices proximate the user, an ambient noise level, an ambient light level, and/or a time of day. It should be appreciated that the collected data may be stored locally on the mobile device and/or transmitted to another computing device such as a server.

In act 206, the mobile device may identify a behavior based on collected sensor information. In some embodiments, the mobile device may identify a behavior based on sensor information indicative of at least one parameter of the user, such as a movement of a body part of the user, a blood pressure of the user, a body temperature of the user, a galvanic skin response of the user, and/or an oxygen saturation of the user. In these embodiments, the mobile device may compare the information indicative of at least one parameter of the user with a model of a particular behavior, such as smoking, to determine whether the user engaged in the behavior. For example, the mobile device may receive information from an accelerometer disposed about a wrist of the user. In this example, the mobile device may compare the output of the accelerometer with a model of the wrist movements during a smoking behavior to determine whether the user is smoking.

In act 208, the mobile device may obtain contextual information regarding the identified behavior. In some embodiments, the mobile device may obtain the contextual information based on the information that is indicative of the at least one parameter of an environment of the user, such as a location of the user, individuals that are proximate the user, an ambient noise level, an ambient light level, and/or a time of day. For example, the mobile device may receive a location of the user when the user is engaging in a particular behavior, such as smoking, and may identify a nearby landmark based on the location, such as a home of the user, a workplace of the user, a restaurant, and a store. In another example, the mobile device may receive information indicative of the particular BLUETOOTH enabled devices that are within range of the mobile device when the user is engaging a particular behavior, such as using chewing tobacco, and identify the other individuals that are proximate the user based on the information indicative of the nearby BLUETOOTH enabled devices.

In act 210, the mobile device may determine whether intervention is needed based on the identified behavior and/or the contextual information. In some embodiments, the mobile device may determine whether intervention is needed based on one or more rules the each define an action to be performed in response to detecting one or more conditions. For example, a rule may indicate that the mobile device should display an encouraging message to the user at a particular time in the evening when the user usually smokes a cigarette. In this example, the mobile device may determine that intervention is needed responsive to the time of day, such as the time of day identified in act 208, matches the time of day in the rule and proceed to act 212 to intervene by displaying the encouraging message. Otherwise, the mobile device may determine that the conditions in the rule were not met and return to act 204 to continue monitoring the sensor(s). It should be appreciated that the rules may be generated locally by the mobile device and/or a server in communication with the mobile device based on analysis of previous identified behaviors and associated contextual information. Further, the rules may be generated with the assistance of input from a health coach. For example, a server in communication with the mobile device may display a web interface to the health coach and permit the health coach to specify particular rules and/or adjust existing rules.

In act 212, the mobile device may intervene with the user to discourage (or encourage) a particular behavior. For example, the mobile device may display a message to the user, vibrate, sound an alert, and/or initiate a phone call to a health coach. In another example, the mobile device may perform an action to distract the user such as play music, open a game, and/or initiate a conversation with a friend by sending a text message. In some embodiments, the mobile device may perform the action in a particular rule that triggered the mobile device to determine that intervention was needed in act 210. For example, the mobile device may determine that the particular conditions for a rule have been met and the mobile device may perform the action associated with that rule in act 212.

The processes described above are illustrative embodiments and are not intended to limit the scope of the present disclosure. The acts in the processes described above may be ordered in any suitable way. Accordingly, embodiments may be constructed in which acts are performed in an order different than illustrated, which may include performing some acts simultaneously, even though shown as sequential acts in illustrative embodiments. Further, one or more acts described may be omitted and/or other acts may be added.

Various aspects and functions described herein may be implemented as specialized hardware or software components executing in one or more specialized computer systems, such as server 102, mobile device 104, and/or a wearable device including a wearable sensor 106. There are many examples of computer systems that are currently in use that could be specially programmed or specially configured. These examples include, among others, network appliances, personal computers, workstations, mainframes, networked clients, servers, media servers, application servers, database servers, and web servers. Other examples of computer systems may include mobile computing devices (e.g., smartphones, tablet computers, and personal digital assistants) and network equipment (e.g., load balancers, routers, and switches). Examples of particular models of mobile computing devices include iPhones, iPads, and iPod Touches running iOS operating systems available from Apple, Android devices like Samsung Galaxy Series, LG Nexus, and Motorola Droid X, Blackberry devices available from Blackberry Limited, and Windows Phone devices. Further, aspects may be located on a single computer system or may be distributed among a plurality of computer systems connected to one or more communications networks.

Figure 3:
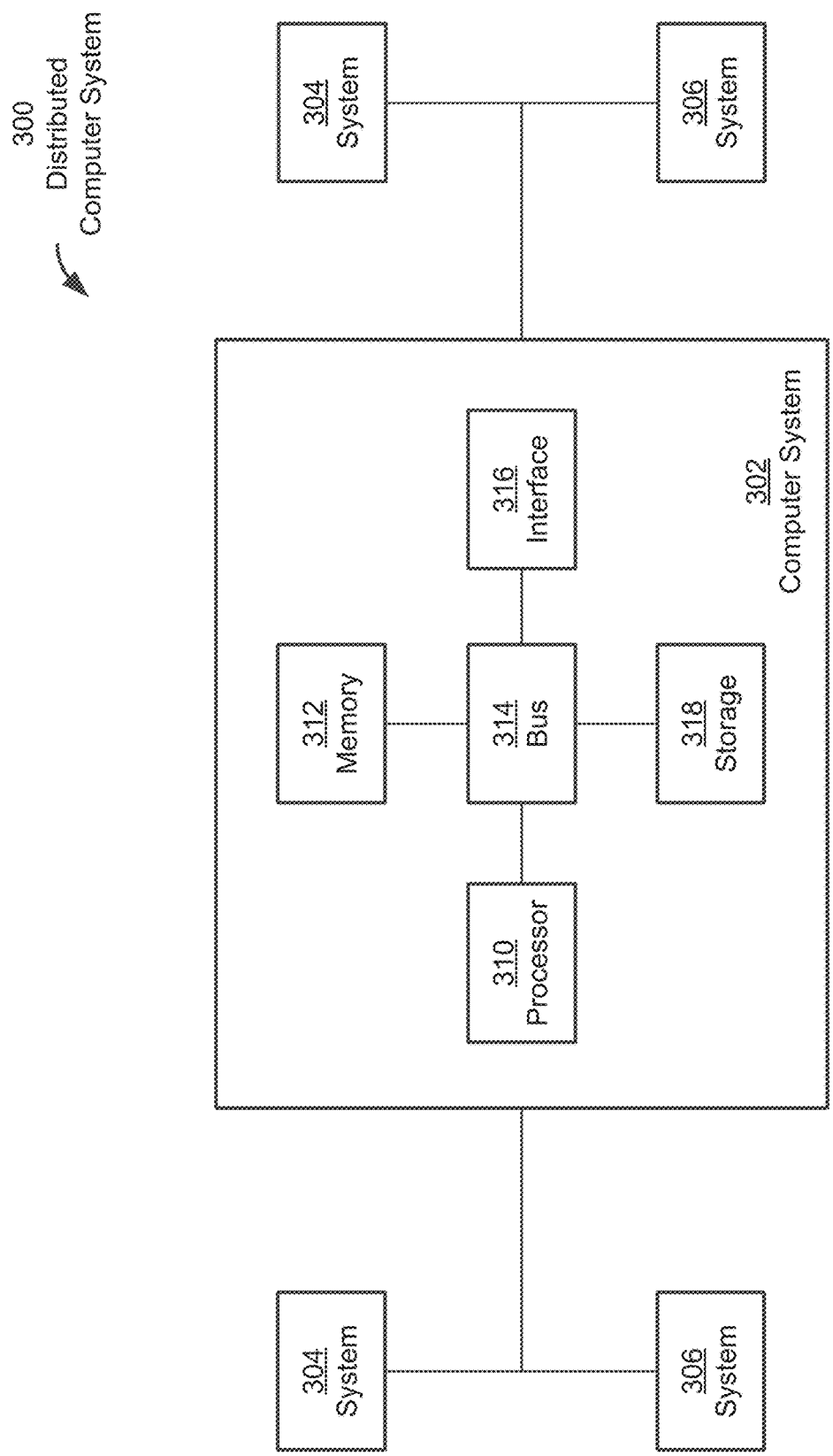
FIG. 3 is a block diagram of an example computer system, according to some embodiments.

For example, various aspects, functions, and processes may be distributed among one or more computer systems configured to provide a service to one or more client computers, or to perform an overall task as part of a distributed system, such as the distributed computer system 300 shown in FIG. 3. Additionally, aspects may be performed on a client-server or multi-tier system that includes components distributed among one or more server systems that perform various functions. Consequently, embodiments are not limited to executing on any particular system or group of systems. Further, aspects, functions, and processes may be implemented in software, hardware or firmware, or any combination thereof. Thus, aspects, functions, and processes may be implemented within methods, acts, systems, system elements and components using a variety of hardware and software configurations, and examples are not limited to any particular distributed architecture, network, or communication protocol.

Referring to FIG. 3, there is illustrated a block diagram of a distributed computer system 300, in which various aspects and functions are practiced. As shown, the distributed computer system 300 includes one or more computer systems that exchange information. More specifically, the distributed computer system 300 includes computer systems 302, 304, and 306. As shown, the computer systems 302, 304, and 306 are interconnected by, and may exchange data through, a communication network 308. The network 308 may include any communication network through which computer systems may exchange data. To exchange data using the network 308, the computer systems 302, 304, and 306 and the network 308 may use various methods, protocols and standards, including, among others, Fiber Channel, Token Ring, Ethernet, Wireless Ethernet, Bluetooth, IP, IPV6, TCP/IP, UDP, DTN, HTTP, FTP, SNMP, SMS, MMS, SS7, JSON, SOAP, CORBA, REST, and Web Services. To ensure data transfer is secure, the computer systems 302, 304, and 306 may transmit data via the network 308 using a variety of security measures including, for example, SSL or VPN technologies. While the distributed computer system 300 illustrates five networked computer systems, the distributed computer system 300 is not so limited and may include any number of computer systems and computing devices, networked using any medium and communication protocol.

As illustrated in FIG. 3, the computer system 302 includes a processor 310, a memory 312, an interconnection element 314, an interface 316 and data storage element 318. To implement at least some of the aspects, functions, and processes disclosed herein, the processor 310 performs a series of instructions that result in manipulated data. The processor 310 may be any type of processor, multiprocessor or controller. Example processors may include a commercially available processor such as an Intel Xeon, Itanium, Core, Celeron, or Pentium processor; an AMD Opteron processor; an Apple A4 or A5 processor; a Sun UltraSPARC processor; an IBM Power5+ processor; an IBM mainframe chip; or a quantum computer. The processor 310 is connected to other system components, including one or more memory devices 312, by the interconnection element 314.

The memory 312 stores programs (e.g., sequences of instructions coded to be executable by the processor 310) and data during operation of the computer system 302. Thus, the memory 312 may be a relatively high performance, volatile, random access memory such as a dynamic random access memory ("DRAM") or static memory ("SRAM"). However, the memory 312 may include any device for storing data, such as a disk drive or other nonvolatile storage device. Various examples may organize the memory 312 into particularized and, in some cases, unique structures to perform the functions disclosed herein. These data structures may be sized and organized to store values for particular data and types of data.

Components of the computer system 302 are coupled by an interconnection element such as the interconnection element 314. The interconnection element 314 may include any communication coupling between system components such as one or more physical busses in conformance with specialized or standard computing bus technologies such as IDE, SCSI, PCI and InfiniBand. The interconnection element 314 enables communications, including instructions and data, to be exchanged between system components of the computer system 302.

The computer system 302 also includes one or more interface devices 316 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 302 to exchange information and to communicate with external entities, such as users and other systems.

The data storage element 318 includes a computer readable and writeable nonvolatile, or non-transitory, data storage medium in which instructions are stored that define a program or other object that is executed by the processor 310. The data storage element 318 also may include information that is recorded, on or in, the medium, and that is processed by the processor 310 during execution of the program. More specifically, the information may be stored in one or more data structures specifically configured to conserve storage space or increase data exchange performance. The instructions may be persistently stored as encoded signals, and the instructions may cause the processor 310 to perform any of the functions described herein. The medium may, for example, be optical disk, magnetic disk or flash memory, among others. In operation, the processor 310 or some other controller causes data to be read from the nonvolatile recording medium into another memory, such as the memory 312, that allows for faster access to the information by the processor 310 than does the storage medium included in the data storage element 318. The memory may be located in the data storage element 318 or in the memory 312, however, the processor 310 manipulates the data within the memory, and then copies the data to the storage medium associated with the data storage element 318 after processing is completed. A variety of components may manage data movement between the storage medium and other memory elements and examples are not limited to particular data management components. Further, examples are not limited to a particular memory system or data storage system.

Although the computer system 302 is shown by way of example as one type of computer system upon which various aspects and functions may be practiced, aspects and functions are not limited to being implemented on the computer system 302 as shown in FIG. 3. Various aspects and functions may be practiced on one or more computers having a different architectures or components than that shown in FIG. 3. For instance, the computer system 302 may include specially programmed, special-purpose hardware, such as an application-specific integrated circuit ("ASIC") tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 302 may be a computer system including an operating system that manages at least a portion of the hardware elements included in the computer system 302. In some examples, a processor or controller, such as the processor 310, executes an operating system. Examples of a particular operating system that may be executed include a Windows-based operating system, such as, Windows NT, Windows 2000 (Windows ME), Windows XP, Windows Vista or Windows 7, 8, or 10 operating systems, available from the Microsoft Corporation, a MAC OS System X operating system or an iOS operating system available from Apple Computer, one of many Linux-based operating system distributions, for example, the Enterprise Linux operating system available from Red Hat Inc., a Solaris operating system available from Oracle Corporation, or a UNIX operating systems available from various sources. Many other operating systems may be used, and examples are not limited to any particular operating system.

The processor 310 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .Net, SmallTalk, Java, C++, Ada, C # (C-Sharp), Python, or JavaScript. Other object-oriented programming languages may also be used. Alternatively, functional, scripting, or logical programming languages may be used.

Additionally, various aspects and functions may be implemented in a non-programmed environment. For example, documents created in HTML, XML or other formats, when viewed in a window of a browser program, can render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements (e.g., specialized hardware, executable code, data structures or objects) that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user space application) or in a commonly shared data structure (such as an application registry that is defined by an operating system). In addition, some examples provide for both system and user interfaces that allow external entities to modify the parameters and thereby configure the behavior of the components.

Based on the foregoing disclosure, it should be apparent to one of ordinary skill in the art that the embodiments disclosed herein are not limited to a particular computer system platform, processor, operating system, network, or communication protocol. Also, it should be apparent that the embodiments disclosed herein are not limited to a specific architecture or programming language.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A health enhancement system, the system comprising:
   a wearable sensor configured to generate first type information indicative of at least one parameter of a user;
   a mobile device comprising:
      at least one processor communicatively coupled to the wearable sensor; and
      at least one computer-readable storage medium storing instructions which program the at least one processor to:
         receive the first type information indicative of at least one parameter of the user;
         identify a behavior performed by the user based on the first type information indicative of at least one parameter of the user;
         obtain contextual information comprising first values of second type information, wherein the first values are correlated with the identified behavior;
         store the obtained contextual information;
         detect a plurality of patterns in the stored contextual information;
         obtain further values of the second type information;
         determine whether to intervene based on at least correspondence between a respective detected pattern of the plurality of detected patterns and the further values of the second type information; and
         intervene with the user responsive to a determination to intervene, wherein intervening comprises generating a human perceptible output configured to encourage or discourage a future action of the user such that timing of the human perceptible output is based on the correspondence between the respective detected pattern and the further values of the second type information, and wherein content of the human perceptible output is selected based on the correspondence between the respective detected pattern and the further values of the second type information.

2. The system of claim 1, wherein the mobile device is a wearable device and wherein the wearable sensor is integrated into the wearable device.

3. The system of claim 1, wherein the wearable sensor includes at least one of: an accelerometer, a blood pressure sensor, a pulse oximeter, a galvanic skin response sensor, and a body temperature sensor.

4. The system of claim 1, wherein the identified behavior includes at least one of: smoking, using chewing tobacco, consuming alcohol, and overeating.

5. The system of claim 1, wherein the mobile device includes a sensor configured to generate information indicative of at least one parameter of an environment of the user and wherein the at least one processor of the mobile device is further programmed to obtain the contextual information regarding the identified behavior from the information indicative of at least one parameter of the environment of the user.

6. The system of claim 5, wherein the sensor includes a global positioning system (GPS) receiver and wherein the contextual information includes a location of the user when the user engaged in the identified behavior.

7. The system of claim 5, wherein the sensor includes a time-keeping device and wherein the contextual information includes a time of day when the user engaged in the identified behavior.

8. The system of claim 1, wherein the at least one processor of the mobile device is further programmed to:
   determine whether to intervene at least in part by comparing a rule defining an action to be performed in response to detecting one or more conditions to at least one of the identified behavior and the contextual information regarding the identified behavior; and
   intervene with the user at least in part by performing the action in the rule.

9. The system of claim 8, further comprising a server in communication with the mobile device and being configured to generate the rule and transmit the rule to the mobile device, wherein the mobile device is configured to transmit the identified behavior and the contextual information regarding the identified behavior to the server and wherein the server is further configured to generate the rule based on the identified behavior and the contextual information regarding the identified behavior.

10. The system of claim 1, wherein the mobile device further includes a display coupled to the at least one processor and wherein the at least one processor of the mobile device is further programmed to intervene with the user at least in part by displaying a message via the display.

11. A method of enhancing a health of a user, the method comprising:
sensing, by a wearable sensor, first type information indicative of at least one parameter of the user;
identifying, by a computing device in communication with the wearable sensor, a behavior performed by the user based on the first type information indicative of at least one parameter of the user;
obtaining, by the computing device, contextual information comprising first values of second type information, wherein the first values are correlated with the identified behavior;
identifying a trigger condition for the behavior based at least in part on a pattern in the obtained contextual information;
obtain further values of the second type information;
determining, by the computing device, whether to intervene based on at least detecting the trigger condition from the further values of the second type information; and
intervening, by the computing device, with the user responsive to a determination to intervene, wherein intervening comprises:
selecting a human perceptible output based on the detected trigger condition; and
generating the human perceptible output configured to encourage or discourage a future action of the user, such that timing and content of the human perceptible output are based on the detected trigger condition.

12. The method of claim 11, wherein the wearable sensor includes at least one of: an accelerometer, a blood pressure sensor, a pulse oximeter, a galvanic skin response sensor, and a body temperature sensor.

13. The method of claim 11, wherein the identified behavior includes at least one of: smoking, using chewing tobacco, overeating.

14. The method of claim 11, further comprising sensing at least one parameter of an environment of the user by a sensor and wherein obtaining the contextual information regarding the identified behavior includes obtaining the contextual information regarding the identified behavior from the information indicative of at least one parameter of the environment of the user.

15. The method of claim 14, wherein the sensor includes a global positioning system (GPS) receiver and wherein the contextual information includes a location of the user when the user engaged in the identified behavior.

16. The method of claim 14, wherein the sensor includes a time-keeping device and wherein the contextual information includes a time of day when the user engaged in the identified behavior.

17. The method of claim 11, wherein generating a human perceptible output comprises activating a buzzer in a portable device used by the user.

18. A health enhancing system, the system comprising:
a wearable device configured to be disposed about a wrist of a user, the wearable device comprising an accelerometer configured to generate information indicative of a movement of the user's wrist;
a mobile device comprising:
at least one processor communicatively coupled to the wearable device;
a display coupled to the at least one processor;
a sensor coupled to the at least one processor and configured to generate information indicative of at least one parameter of an environment of the user; and
at least one computer-readable storage medium storing instructions which program the at least one processor to:
receive the information indicative of the movement of the user's wrist;
identify a smoking behavior performed by the user based on the information indicative of the movement of the user's wrist;
record as contextual information regarding the identified smoking behavior first values of at least one parameter of the environment of the user correlated with identifying the smoking behavior;
determine whether to intervene based on a correspondence between the recorded contextual information and second values of the at least one parameter of the environment of the user; and
intervene with the user at least in part by displaying a message via the display responsive to a determination to intervene, wherein the message is configured to discourage the user from engaging in the smoking behavior at a future time and timing and content of the message is selected based on a trigger condition associated with the first values.

19. The system of claim 1, wherein the system further comprises:
at least one computer-readable storage medium configured to store a plurality of trigger conditions for the behavior and associated actions;
the at least one processor is configured to:
detect the plurality of patterns in the stored contextual information and, based thereon, storing the plurality of trigger conditions in the computer-readable storage medium in conjunction with respective actions for the plurality of trigger conditions; and
generate the human perceptible output based on the action associated with the detected trigger condition in the computer-readable storage medium, such that the timing and type of intervention employed is based on the detected trigger condition.

20. The method of claim 11, wherein:
the method further comprises receiving input though a user interface indicating an associated action for an identified trigger condition; and
the timing and type of intervention employed is based on the detected trigger condition based on generating the human perceptible output by selecting the output based on an action associated with the detected trigger condition.

* * * * *